United States Patent [19]

Barnett

[11] Patent Number: 4,545,235

[45] Date of Patent: Oct. 8, 1985

[54] GAS ANALYZER WITH ASPIRATED TEST GAS

[75] Inventor: Daniel C. Barnett, Concord Township, Lake County, Ohio

[73] Assignee: The Babcock & Wilcox Company, New Orleans, La.

[21] Appl. No.: 609,673

[22] Filed: May 14, 1984

[51] Int. Cl.[4] ............................................. G01D 18/00
[52] U.S. Cl. ..................................................... 73/1 G
[58] Field of Search ............... 73/1 G, 863.83, 863.84, 73/863.86, 23

[56] References Cited

U.S. PATENT DOCUMENTS

| | | | |
|---|---|---|---|
| 2,586,313 | 2/1952 | Dwyer | 73/23 X |
| 3,427,862 | 2/1969 | Hübner | 73/23 |
| 3,495,437 | 2/1970 | Estes III, et al. | 73/1 G |
| 4,094,187 | 6/1978 | Nauarre, Jr. | 73/1 G |
| 4,322,964 | 4/1982 | Melgaard et al. | 73/1 G |

FOREIGN PATENT DOCUMENTS

| | | | |
|---|---|---|---|
| 74438 | 6/1980 | Japan | 73/1 G |
| 19533 | 2/1983 | Japan | 73/23 |

OTHER PUBLICATIONS

"A Versatile Pneumatic Instrument Based on Critical Flow"; *The Review of Scientific Insturments;* vol. 21, No. 1; Jan. 1950; pp. 25-30; W. A. Wildhock

*Primary Examiner*—Stewart J. Levy
*Assistant Examiner*—Tom Noland
*Attorney, Agent, or Firm*—Vytas R. Matas; Robert J. Edwards

[57] ABSTRACT

A gas analyzer arrangement and method of operating the arrangement comprise a probe which extends from a test space containing a sample gas, to an input line which is connected to an analyzer for analyzing the sample gas. An output line is connected to the analyzer for discharging gas from the analyzer. An aspirator is used in the output line for drawing sample gas from the test space through the analyzer. For calibration, a second aspirator is provided in the input line for equalizing the flow in the input and the output lines to stop the flow of sample gas through the analyzer. After the flow is equalized and thus reduced to zero, a test gas is supplied to the input line at the same selected flow rate as the sample gas was supplied through the analyzer. The test gas is used for calibrating the analyzer.

6 Claims, 3 Drawing Figures

GAS ANALYZER WITH ASPIRATED TEST GAS

FIELD AND BACKGROUND OF THE INVENTION

The present invention relates, in general, to gas analyzers for analyzing the presence and/or quantity of a gas, and in particular to a new and useful arrangement and method of calibrating gas analyzers using a test gas of known properties.

Gas analyzers are known which use aspirators that function to draw a sample gas from an environment, for example from the interior of a gas duct, and bring that sample to a sensor or other sampling system which performs an analytical test on the sample.

The sample gas is drawn by a probe to the sensor or sampling system. Such probes usually extend into the environment to be tested and are used in conjunction with a filter for filtering out debris.

Such gas analyzers are known to require some mechanism for applying a test gas in order to accurately check the calibration of the instrument. Simply flooding the system with the test gas to overcome the sample gas entering the probe is not an accurate check since this pressurizes the system which is normally operated at negative pressure.

Such a method also cannot check for the existence of leaks in the normally negatively pressurized system.

Such a method also produces more flow rate through the sensor cavities which will represent an error particularly in certain types of sensors which are sensitive to flow rate. This would also represent an error in sensors which utilize a test gas that is diluted with air at constant flow, for example in the case of carbon monoxide sensors which require dilution air for combustion of the catalyst.

Other methods of calibrating a gas analyzer include physically blocking the probe to prevent entry of the sample gas and to prevent mixing between the sample gas and the test gas. This is usually accomplished by physically inserting a plug into the probe or into a connecting passage for the probe. The test gas is then injected into a port in the sampling or analyzing system which is downstream of the mechanical plug. Shortcomings of this method include frequent failures of seals used to block off the same probe or failures in seals associated with shafts used for moving the plug assembly for plugging the probe. Other problems include seizing between two relatively movable parts where metal to metal thread seals are utilized. This is due to the high temperatures required by some sampling systems, as well as high temperatures which may exist in the duct or environment containing the sample gas. In addition to the foregoing problems, the prior art methods require a local calibration unless a solenoid shut-off is used which is also effected by high temperatures and require seals.

SUMMARY OF THE INVENTION

According to the invention, a reverse aspirator for administering test gas is utilized to block the flow of sample through the analyzer without the use of mechanical moving parts. At the same time, the test gas is supplied to the analyzer at the same pressure and flow rate at which the sample gas was applied, to avoid problems associated with a method utilizing a pressurized test gas.

Advantages of the invention include the lack of any moving parts or seals, the lack of any mechanical probe shut-off devices and the fact that high ambient and operating temperatures do not adversely affect the inventive technique.

Accordingly, an object of the invention is to provide a method of operating a gas analyzer for analyzing a sample gas from a test space, comprising, supplying the sample gas to be analyzed at a selected flow rate to the gas analyzer from the test space over a probe extending into the test space and over an input line connected between the probe and the analyzer, discharging the sample gas from the analyzer over an output line, equalizing a pressure in the input line with a pressure in the output line to stop the supply of sample gas to the analyzer, and supplying a test gas for use in calibrating the analyzer at the selected flow rate to the analyzer over the input line.

A further object of the invention is to provide an arrangement for analyzing a sample gas from a test space comprising a probe extending into the space, an input line connected to the probe, gas analyzer means connected to the input line for receiving a sample gas from the test space over the probe and the input line, an output line connected to the gas analyzer means for discharging gas from the analyzer means, means for equalizing a pressure in the input line with a pressure in the output line to prevent a flow of gas through the gas analyzer means and means for applying a test gas at a selected flow rate to the input line which is equal to a flow rate of a sample gas through the input line, for calibrating the gas analyzer means.

A further object of the invention is to provide an arrangement for analyzing a sample gas and for calibrating a gas analyzer for the sample gas which is simple in design, rugged in construction and economical to manufacture.

For an understanding of the principles of the invention, reference is made to the following description of a typical embodiment thereof as illustrated in the accompanying drawing.

DESCRIPTION OF THE PREFERRED EMBODIMENT

Figure 1:
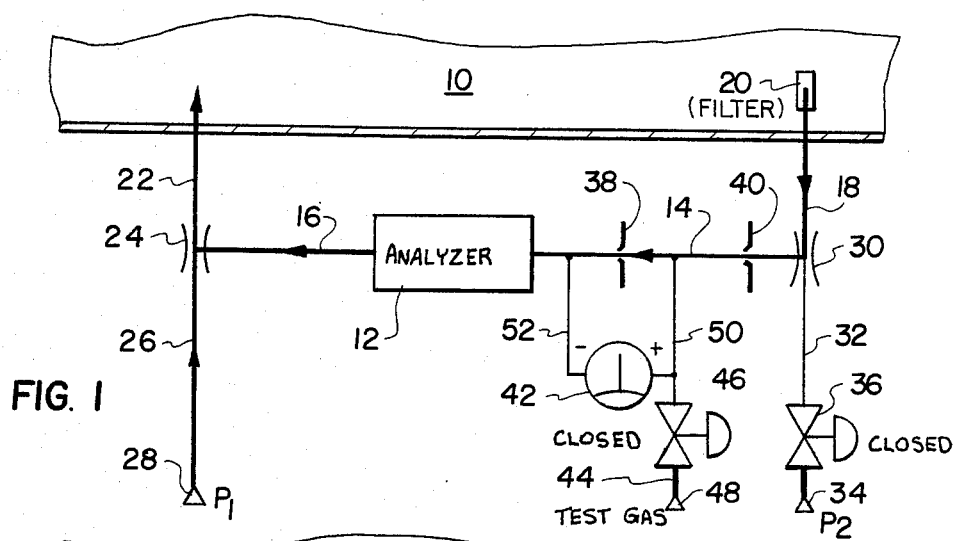
FIG. 1 is a schematic block diagram showing the gas analyzer arrangement in operation to analyze a sample gas.

Referring to the drawings, in particular, the invention embodied in FIG. 1 comprises a gas analyzer arrangement for analyzing a sample gas from a test space 10 which may be the interior of a known process or a conduit for carrying a gas sample such as exhaust from a combustion process. The arrangement utilizes a gas analyzer 12 which is of known design and which includes an input line 14 for supplying a sample gas to the sensor and an output line 16 for discharging sample gas from the sensor.

A probe 18, which is also of known design, has an open input end which is covered by a filter 20 and extends into the test space 10. A return line 22 is connected between the output line 16 and the test space 10 for returning the tested sample gas to the test space.

In accordance with one feature of the invention, a sample aspirator 24, which itself is of known design, has a power input line 26 connected to a source of pressure 28 which is at level $P_1$. An orifice of sample aspirator 24 is connected to the output line 16 so that, depending on the pressure $P_1$ in power line 26, a selected flow rate will be established on output line 16. The sample gas as well as the powering gas is discharged over line 22 into the test space 10. This flow rate also induces a flow of sample gas, at the same flow rate, over input line 14, which draws sample gas from test space 10, through filter 20 and probe 18.

In accordance with another feature of the invention, a test gas aspirator 30 is connected between probe 18 and input line 14. Aspirator 30 is of similar design to aspirator 24 and is powered by a second power line 32 connected to a second source of pressure 34 which provides a pressure $P_2$. Power line 32 is isolated from source 34 by a power line valve 36.

Input line 14 is provided with a first orifice 38 and a second orifice 40. A pressure gauge 42 for measuring the pressure drop across orifice 38 is connected to the input line 14 upstream and downstream of the first orifice 38. The change in pressure $\Delta P$ is measured in inches of water. This pressure drop across orifice 38 is proportional to the selected flow rate and thus can be utilized as a measurement for the flow rate.

Connected to the upstream side of pressure gauge 42 is a test gas line 44 which includes a test gas valve 46 and is connected to a source of test gas at 48.

FIG. 1 illustrates the flow of sample gas through analyzer 12 for analyzing the sample gas. In this measuring condition for the analyzer arrangement, power line valve 36 and test gas valve 46 are closed. The flow rate as measured by a pressure gauge 42 is determined by pressure $P_1$ on power line 26 through aspirator 24.

Figure 2:
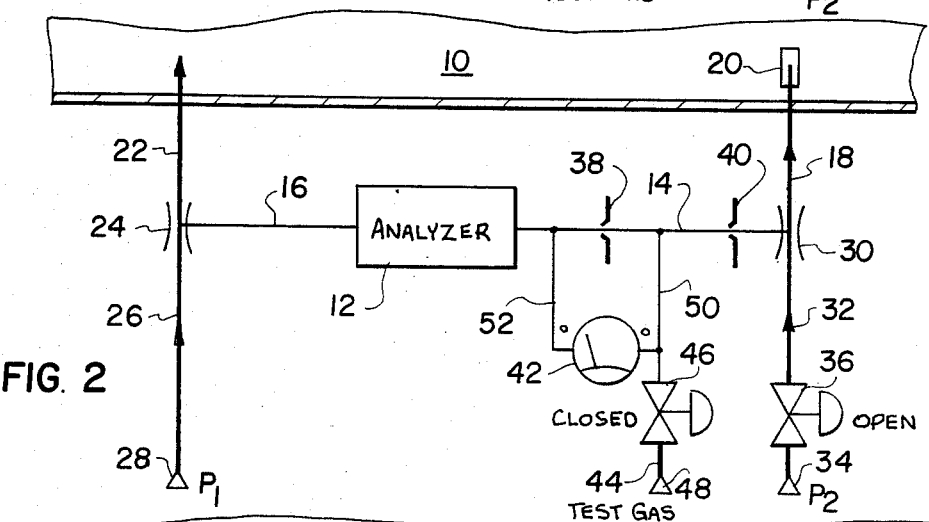
FIG. 2 is a view similar to FIG. 1 showing the arrangement in a position which is preparatory for a calibration of the gas analyzer.

FIG. 2 shows a flow condition when the analyzer 12 is being prepared for calibration. In this condition of the arrangement, valve 36 is opened allowing the aspirator 30 to draw gas until the aspirator 30, powered by pressure $P_2$ is since this pressure is an indication of flow across the orifice 38 drawing gas from input line 14 at the same rate as aspirator 24 is capable of drawing gas from output line 16. The pressures in the input and output line are then equalized and no gas then flows through analyzer 12. The pressure drop as indicated by pressure gauge 42 drops to zero since there is no flow in the input line 14 and thus no pressure drop across orifice 38 at a point capable of.

Figure 3:
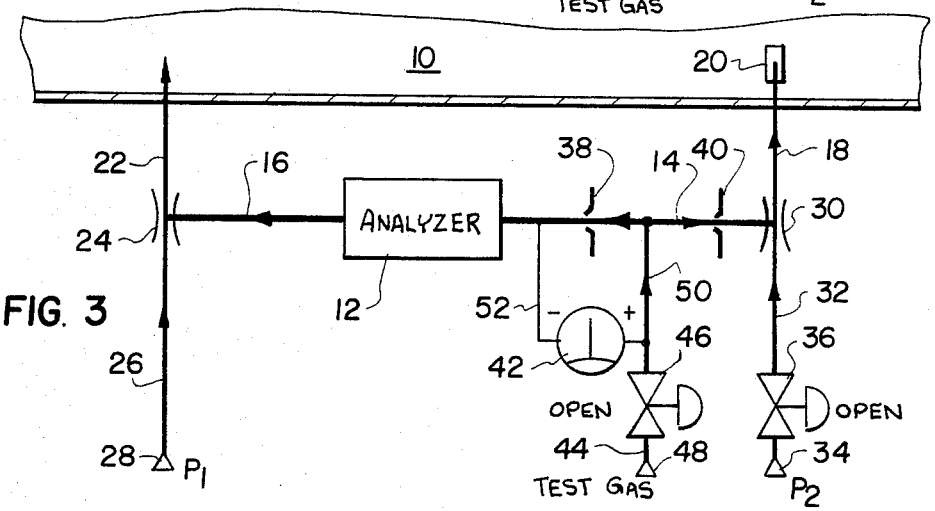
FIG. 3 is a view similar to FIG. 1 of the arrangement in a position for calibrating the gas analyzer.

At this point, as illustrated in FIG. 3, test gas valve 46 is opened by a selected amount and supplies test gas over upstream line 50 to the input line 14. Test gas flows in both directions over orifices 38 and 40. The valve 46 is opened until the flow rate, indicated on pressure gauge 42, is equal to the selected flow rate for the sample gas illustrated in FIG. 1. Test gas is thus supplied to analyzer 12 under the same conditions as the sample gas was provided to the analyzer so that unambiguous calibration can take place.

Test gas also flows in the reverse direction on line 14 through the aspirator 30 back to the test space 10 but this does not adversely affect the calibration step.

While specific embodiments of the invention have been shown and described in detail to illustrate the application of the principles of the invention, it will be understood that the invention may be embodied otherwise without departing from such principles.

What is claimed is:
1. A method of operating a gas analyzer for analyzing a sample gas from a test space, comprising:
   supplying the sample gas to be analyzed at a selected flow rate to the gas analyzer over a probe extending into the test space and over an input line connected between the probe and the analyzer;
   discharging the sample gas from the analyzer over an output line;
   equalizing a flow in the input line with a flow in the output line so as to stop the supply of sample gas to the analyzer; and
   supplying a test gas to be used in calibrating the analyzer at the selected flow rate to the analyzer over the input line whereby test gas is discharged over the output line;
   the sample gas at the selected flow rate supplied by powering a sample aspirator connected to the output line; and
   the flow in the input and output lines equalized by powering a test gas aspirator connected to the input line.

2. A method according to claim 1, wherein a, pressure drop across a first orifice provided in the input line is measured to determine the selected flow rate for the sample gas, the test gas aspirator is powered until the pressure drop across the first orifice drops to zero, and the test gas is supplied to the input line upstream of the first orifice at a rate to return the pressure drop across the first orifice to a level corresponding to the selected flow rate.

3. A gas analyzer arrangement for analyzing a sample gas from a test space, comprising:
   a probe extending into the test space;
   an input line connected to said probe;
   a gas analyzer connected to said input line for receiving gas to be sampled from said input line;
   an output line for discharging gas from said analyzer;
   sample aspiration means connected to said ouput line for drawing sample gas from the test space through said probe and through said input line, to said analyzer and through said output line;
   test gas aspiration means connected to said input line for equalizing a flow of gas in said input line with a flow of gas in said output line for stopping a flow of gas through said analyzer;
   flow measuring means connected to said input line for measuring a flow in said input line; and
   test gas supply means connected to said input line for supplying test gas to said input line at the selected flow rate for calibration of said analyzer.

4. An arrangement according to claim 3, wherein said sample aspiration means comprises an aspirator having a power input connected to a source of pressure and a sample input connected to said output line, said test gas aspiration means comprising an aspirator having a power line for receiving a source of pressure and connected to said input line;
   said power line having a valve therein for adjusting the flow through said test gas aspirator.

5. An arrangement according to claim 4, wherein said flow measuring means comprises a first orifice connected in said input line and a pressure gauge connected between an upstream side and a downstream side of said orifice and to said input line, said test gas supply means connected to said upstream side of said orifice.

6. An arrangement according to claim 5, including a second orifice in said input line upstream of said first orifice and upstream of said pressure gauge.

* * * * *

UNITED STATES PATENT AND TRADEMARK OFFICE
CERTIFICATE OF CORRECTION

PATENT NO. : 4,545,235

DATED : October 8, 1985

INVENTOR(S) : Daniel C. Barnett

It is certified that error appears in the above-identified patent and that said Letters Patent are hereby corrected as shown below:

In column 3, lines 43-44, after "is" cancel "since this pressure is an indication of flow across the orifice 38" and replace with --at a point capable of--.

In column 3, lines 50-51, after "orifice 38" cancel "at a point capable of" and replace with --since this pressure is an indication of flow across the orifice 38--.

In column 4, line 12, after "the analyzer;" delete --and--.

Signed and Sealed this

Eleventh Day of February 1986

[SEAL]

Attest:

Attesting Officer

DONALD J. QUIGG

Commissioner of Patents and Trademarks